United States Patent
Katzlinger et al.

(10) Patent No.: US 10,116,356 B2
(45) Date of Patent: Oct. 30, 2018

(54) SYSTEM AND METHOD FOR OPERATING A MICROPLATE READER

(71) Applicant: Molecular Devices (Austria) GmbH, Wals (AT)

(72) Inventors: Michael Katzlinger, Eugendorf (AT); Georg Kronberger, Salzburg (AT); Bernhard Schinwald, Mundafing (AT)

(73) Assignee: Molecular Devices (Austria) GmbH (AT)

( * ) Notice: Subject to any disclaimer, the term of this patent is extended or adjusted under 35 U.S.C. 154(b) by 67 days.

(21) Appl. No.: 15/344,808

(22) Filed: Nov. 7, 2016

(65) Prior Publication Data

US 2018/0131414 A1 May 10, 2018

(51) Int. Cl.
| | |
|---|---|
| *H04B 5/00* | (2006.01) |
| *G06K 7/10* | (2006.01) |
| *H04L 29/06* | (2006.01) |
| *H04W 4/00* | (2018.01) |
| *H04W 4/80* | (2018.01) |

(52) U.S. Cl.
CPC ....... *H04B 5/0062* (2013.01); *G06K 7/10366* (2013.01); *H04L 69/18* (2013.01); *H04W 4/008* (2013.01); *H04W 4/80* (2018.02); *G06K 2007/10485* (2013.01)

(58) Field of Classification Search
CPC .......... B01L 2300/02; B01L 2300/021; B01L 2300/022; G06K 7/10366; G06K 2007/10485; H04B 5/0025; H04B 5/0056; H04B 5/0062; H04B 5/0068; H04B 5/0075; H04L 69/18; G01J 1/0223; G01J 1/0228; G01J 1/0238; G01J 3/00; G01J 3/0275; H01J 49/0409; H04W 4/80; H04W 4/00; H04W 4/008; H04W 4/50; Y10S 977/853; Y10T 436/112499; Y10Y 436/113332
USPC ........ 340/572.1–572.8, 10.1–10.6; 455/41.1, 455/41.2
See application file for complete search history.

(56) References Cited

U.S. PATENT DOCUMENTS

| | | | | |
|---|---|---|---|---|
| 5,557,544 | A * | 9/1996 | Simon ....................... | G01J 3/02 235/375 |
| 2007/0035732 | A1* | 2/2007 | Marsche ................... | G01J 3/02 356/417 |

OTHER PUBLICATIONS

U.S. Appl. No. 15/138,660 (Nonpublished). Molecular Devices, LLC, filed Apr. 26, 2016 Titled: Methods and Systems for Optical-Based Measurement with Selectable Excitation Light Paths.

(Continued)

*Primary Examiner* — Brian Wilson (57) ABSTRACT

A microplate reader and a method for operating the microplate reader are disclosed. The microplate reader includes a housing, a first NFC reader/writer, a filter tray positioning device, a filter tray, an optical filter disposed in the filter tray, and a controller. The filter tray has a filter tray NFC tag disposed thereon and the filter has a filter NFC tag disposed thereon. The controller receives information about an assay protocol to be undertaken, wherein the assay protocol specifies a filter to be used. The first NFC reader/writer reads filter information stored in the filter NFC tag, the controller directs the NFC reader/writer to store the filter information in the filter tray NFC tag, and the controller enables operation of the microplate reader to undertake the assay protocol only if filter information indicates that the optical filter is in accordance with the filter specified in the assay protocol.

20 Claims, 8 Drawing Sheets

(56) References Cited

OTHER PUBLICATIONS

Purepoint Laser Workstation Product Sheets.
Leica Microsystems "From Eye to Insight", Leica DMi8 with RFID Fluorescence, Copyright by Leica Microsystems CMS GmbH, Wetzlar, Germany, 2015.

* cited by examiner

SYSTEM AND METHOD FOR OPERATING A MICROPLATE READER

FIELD OF DISCLOSURE

The present subject matter relates to microplate reader, and more particularly, to a system and method for validating components used with a microplate reader.

BACKGROUND

A microplate reader is used to detect or measure the response of biological samples to a stimulus disposed on a microplate. The microplate includes a predetermined number of cells configured in a two-dimensional array, and a sample of biological material may be disposed in each cell.

The stimulus may be exposure to radiation (such as light source), a chemical, an electrical field, or an interaction with another biological material. In some cases, the response includes generation of light (for example, if the biological sample fluoresces in response to the stimulus), absorption of particular wavelengths of light, or production of a byproduct. The presence and/or magnitude of one or more such response(s) may be measured using the microplate reader.

Some microplate readers measure only a particular characteristic of the response to stimulus, for example, only emissions due to fluorescence or absorption of light. In contrast, a multi-mode microplate reader measures different characteristics of the responses to a particular stimulus including a change in light absorbance and/or luminescence (fluorescence, chemiluminescence, bioluminescence, electroluminescence, thermoluminescence, and the like) by the sample. Such a multi-mode microplate reader exposes the sample to the stimulus and uses one or more filters to detect the different types of responses.

In addition, the multi-mode microplate reader typically includes apparatus that provides the stimulus to the biological sample including electrical probes and/or one or more micro-pipette(s) for delivering a predetermined amount of one or more reagent(s). The multi-mode microplate reader also includes one or more filters and one or more sensors. Each type of filter allows particular wavelengths of light emitted by the stimulated sample to pass therethrough before being detected by the sensor. The sensor may be photosensor or a digital camera chip, such as a charge-coupled device, a photomultiplier tube, an avalanche photodiode, and the like.

In operation, a user defines an assay protocol that specifies the type of sample to be tested, a layout of the microplate on which samples will be disposed, the stimulation to be provided to each sample, reagents and other material that will be used during testing, and the types of response to be measured. The protocol may associate for each type of response one or more optical filters to position in the light path between the sample and the sensor.

Once the protocol is defined, the microplate reader may be operated to carry out the protocol with one or more microplates. Further, assay kits associated with the protocol may be commercially procured or assembled that include the microplate(s), reagents, and other materials necessary to carry out the protocol. Once developed, the protocol may be stored on a storage media associated with the microplate reader, and retrieved and executed one or more times as necessary For the protocol to be carried out without errors and without interruption, it is important that the filters necessary for the protocol are loaded into the microplate reader, and sufficient quantities of consumable materials that comprise the assay kit associated with the protocol are available.

SUMMARY

According to one aspect, a microplate reader includes a housing, a first NFC reader/writer, a filter tray positioning device, a filter tray, an optical filter disposed in the filter tray, and a controller. A filter tray NFC tag is disposed on the filter tray and the optical filter has a filter NFC tag disposed thereon. The controller receives information about an assay protocol to be undertaken, wherein the assay protocol specifies a filter to be used. The first NFC reader/writer reads filter information stored in the filter NFC tag, the controller directs the NFC reader/writer to store the filter information in the filter tray NFC tag, and the controller enables operation of the microplate reader to undertake the assay protocol only if filter information indicates that the optical filter is in accordance with the filter specified in the assay protocol.

According to another aspect, a method of operating microplate reader that includes a housing, a first NFC reader/writer, and a filter tray positioning device includes the steps of disposing a filter tray in the microplate reader and disposing a first optical filter disposed in the filter tray. The filter tray has an NFC tag disposed thereon and the first optical filter has a first filter NFC tag disposed thereon. The method includes the further steps receiving by a controller information about an assay protocol to be undertaken, wherein the assay protocol specifies a filter to be used, reading the first filter information stored in the first filter NFC tag, and operating the first NFC reader/writer to store the first filter information in the first filter tray tag. In addition, the method includes the step of operating the microplate reader to undertake the assay protocol only if the first filter information indicates that the first optical filter is in accordance with the filter specified by the assay protocol.

Other aspects and advantages will become apparent upon consideration of the following detailed description and the attached drawings wherein like numerals designate like structures throughout the specification.

DETAILED DESCRIPTION

Figure 1:
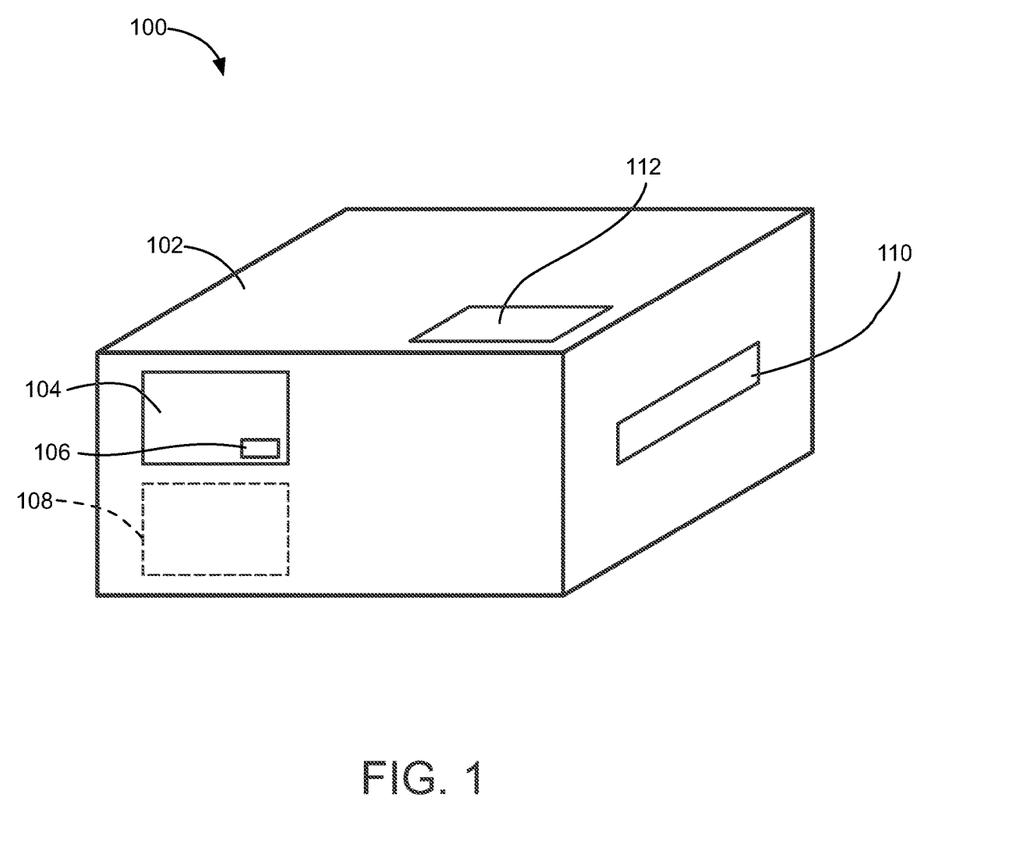
FIG. 1 is an isometric view of a microplate reader in accordance with the present disclosure.

Referring to FIG. 1, a microplate reader 100 includes a housing 102 on which is disposed a display 104 and a first NFC reader/writer 106 adapted for communications with a Near Field Communication (NFC) tag. As should be apparent to one who has skill in the art, an NFC tag typically includes an antenna, an NFC tag, and memory. An NFC reader/writer communicates with the NFC tag to read and/or write information to the memory.

In some embodiments, the display 104 is a touch screen display that allows display of information and entry of commands. In other embodiments, the display 104 may only display information and an external input device may be provided for entry of information. In some embodiments, the NFC reader/write 106 may be separate from the housing 102 of the microplate reader 100 and, for example, may be disposed in a smart phone, tablet, or a computer that is in communications with the microplate reader 100. Such communications may be via a local or a wide area wired or wireless network, Bluetooth, and the like.

The first NFC reader/writer 106 is disposed so that when an NFC tag external to the microplate reader 100 is brought into contact with the first NFC reader/writer 106 or within a predetermined distance of the first NFC reader/writer 106, the first NFC reader/writer 106 communicates with such NFC tag. Although the first NFC reader/writer 106 is shown disposed on the display 104, it should be apparent the first NFC reader/writer 106 may be disposed anywhere on the housing 102 or within the housing 102 of the microplate reader 100 in a position such that first NFC reader/writer 106 is able to communicate with an NFC tag external to the microplate reader 100.

The microplate reader 100 also includes a controller 108, an entry port 110 into which a microplate may be inserted, and one or more ports 112 through which filters and/or reagents used by the microplate reader 100 may be introduced.

Figure 2:
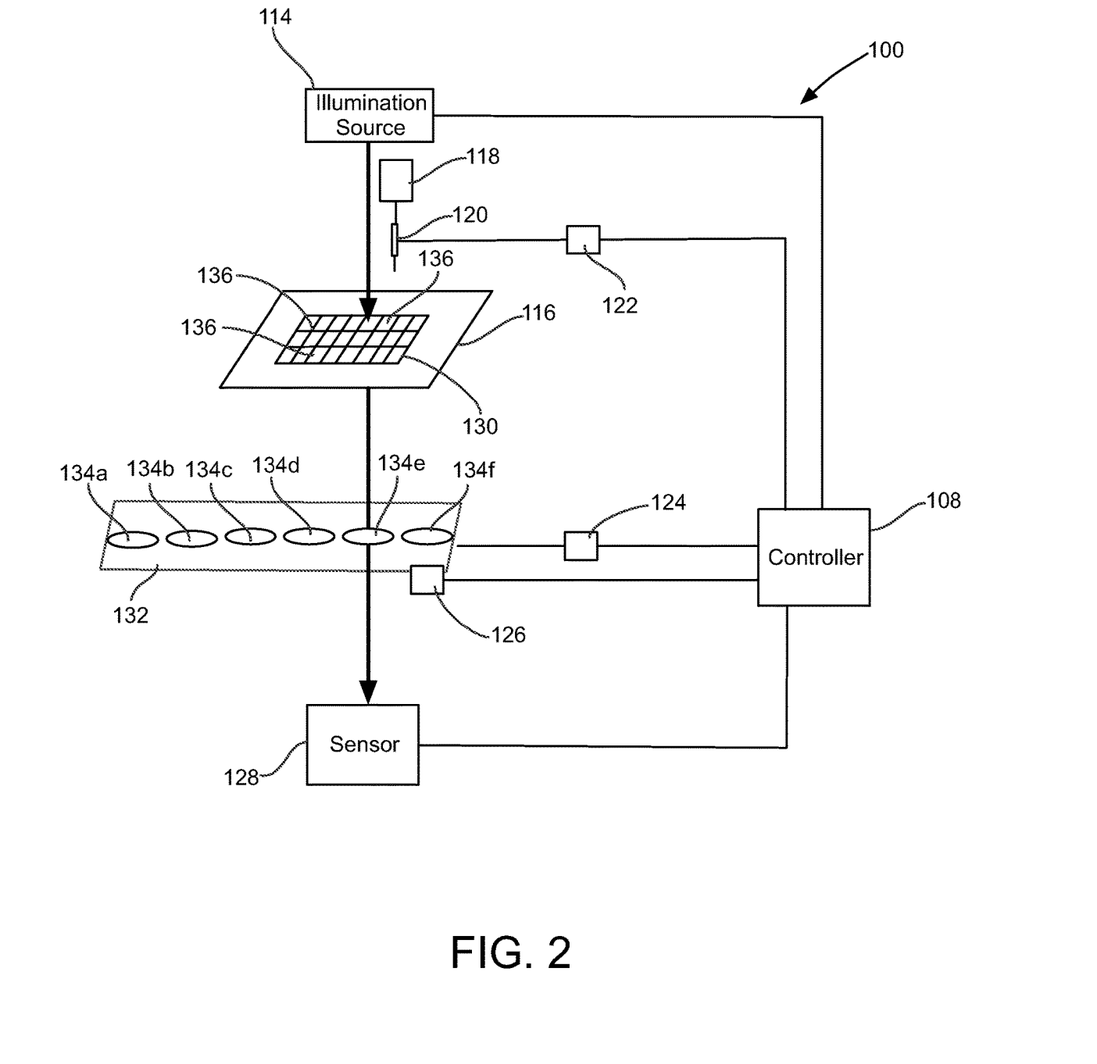
FIG. 2 is a block diagram of the microplate reader of FIG. 1.

Referring to FIG. 2, the microplate reader includes an illumination source 114, a microplate holder 116, one or more reagent supplies 118, one or more micropipettes 120, a micropipette actuation device 122, a filter tray positioning device 124, a second NFC reader/writer 126, and a sensor 128.

During operation, the controller 108 receives an assay protocol to be undertaken and a microplate 130 associated with the protocol is disposed on the microplate holder 116. It should be apparent to one who has ordinary skill in the art, the microplate 130 includes a plurality of wells 136, and a sample may be deposited into each such well 136. Typically, the samples are deposited into the wells 136 before the microplate 130 is inserted into the microplate reader 100.

In addition, a filter tray 132 having a plurality of filters 134a, 134b, . . . , and 134f disposed therein is coupled to the filter tray position device 124. In particular, the filters 134a, 134b, . . . , and 134f are those that are necessary to undertake the protocol. Similarly, each reagent supply 118 necessary to undertake the protocol is fluidically coupled to a respective micropipette 120. In the present disclosure, the term "filter" or as used herein may refer to an optical filter or a monochromator, or any other device that selectively transmits light.

The controller 108 is coupled to the micropipette actuation device 122 and operates motors (not shown) thereof to position one of the micropipettes 120 proximate a selected one of wells 136, and to actuate the micropipette 120 to deposit a reagent from the reagent supply 118 coupled to the micropipette 120 into the selected well 136, as specified by the protocol. Alternately or in addition to using the micropipette actuation device 122, the controller 108 may actuate the illumination source to direct light (or other electromagnetic radiation) toward the selected well 136, in accordance with the protocol.

The controller 108, in accordance with the protocol, operates the filter tray positioning device 124 such that a selected filter 134 in the filter tray 134 is positioned in the light path between the selected well 136 and the sensor 128. Thereafter, light emitted by the sample in the selected well 136 (e.g., because of luminescence) or transmitted through such sample passes through the first filter 134 and is measured by the sensor 128. The sensor 128 measures the intensity of light that falls on one or more receptors thereof, and the controller 108 retrieves such intensity information and records the retrieved information in a storage device (not shown) associated therewith.

The controller 108 may then operate the filter tray positioning device 124 to position the filter tray 132 such that a second filter of the filters 134 is in the light path between the selected well 136 and the sensor 128, and retrieves and records the intensity of light that is detected by the one or more receptors of the sensor 128, as described above.

The controller 108 operates the filter tray positioning device 124 in this manner until light has been passed through all of the filters 134 that are being used. Thereafter, the controller 108 selects another well 136 and undertakes the measurement process described above until all of the wells 136 of the microplate 130 specified by the protocol have been analyzed using the reagents and filters specified by the protocol.

As described in detail below, the first NFC reader/writer 106 and the second NFC reader/writer 126 are used to insure the user has privileges necessary to operate the microplate reader to carry out a particular protocol, and to verify that the correct microplate 130, reagent supplies 118, and filters 134 are provided to the microplate reader 100 to carry out the particular protocol.

Figure 3:
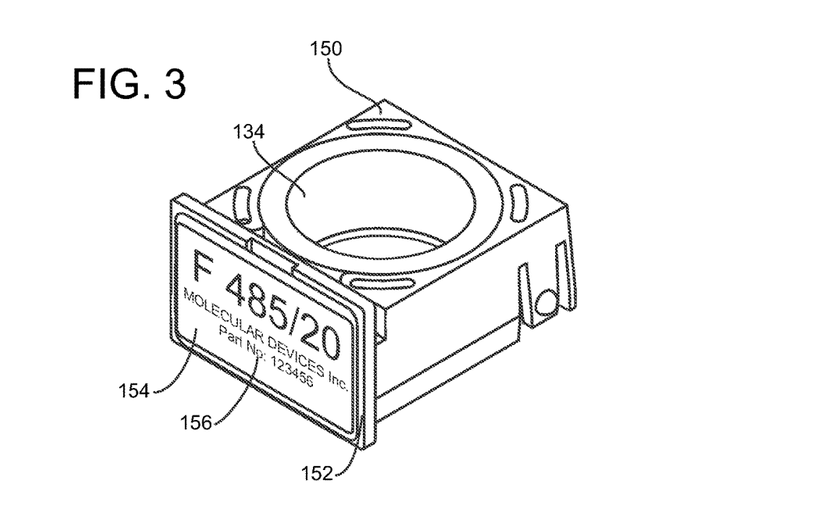
FIG. 3 is an isometric view of a filter holder and a filter that may be used with the microplate reader of FIG. 1.

Referring to FIG. 3, in one embodiment, each filter 134 is disposed in a filter holder 150. Adhesively secured on a face 152 of filter holder 150 is a filter NFC tag 154. The filter NFC tag 154 is integral with a label 156 imprinted with indicia that identifies the filter. Information that identifies the filter 134 is also recorded in the filter NFC tag 154. Such identifying information may include, for example, manufacture, part number, SKU number, wavelength, type, bandwidth, applications, and the like. In some embodiments, the information that identifies the filter 134 is recording in the filter NFC tag 154 when the filter 134 and the filter holder 150 are assembled.

Figure 4:
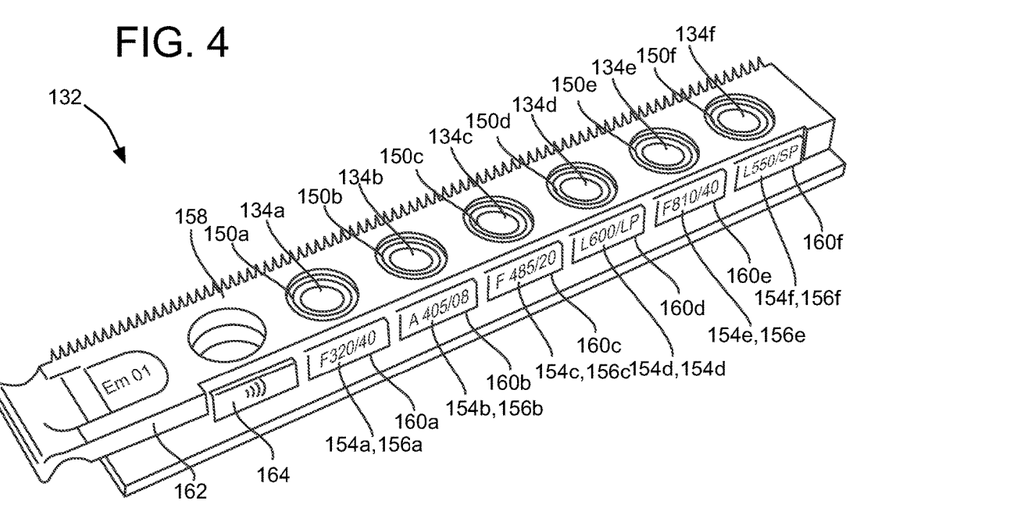
FIG. 4 is an isometric view of a filter tray into which the filter holder and the filter of FIG. 3 may be disposed for user with the microplate reader for FIG. 1.

Referring to FIG. 4, in one embodiment, the filter holders 150a, 150b, . . . and 150f are inserted into corresponding positions of the filter tray 132 such that the filters 134a, 134b, . . . and 134f, respectively, are exposed from a top face 158 of the filter tray 132. Further, when the filter holders 150a, 150b, . . . and 150f are inserted into the filter tray 132 in this manner, the corresponding labels 156a, 156b, . . . and 156f, and therefore the corresponding filter NFC tags 154a, 154b, . . . and 154f, are accessible (i.e., readable by an NFC reader/writer) from respective slots 160a, 160b, . . . and 160f of a front face 162 of the filter tray 132. The filter tray 132 also includes a filter tray NFC tag 164 disposed on the front face 162 thereof.

Figure 5:
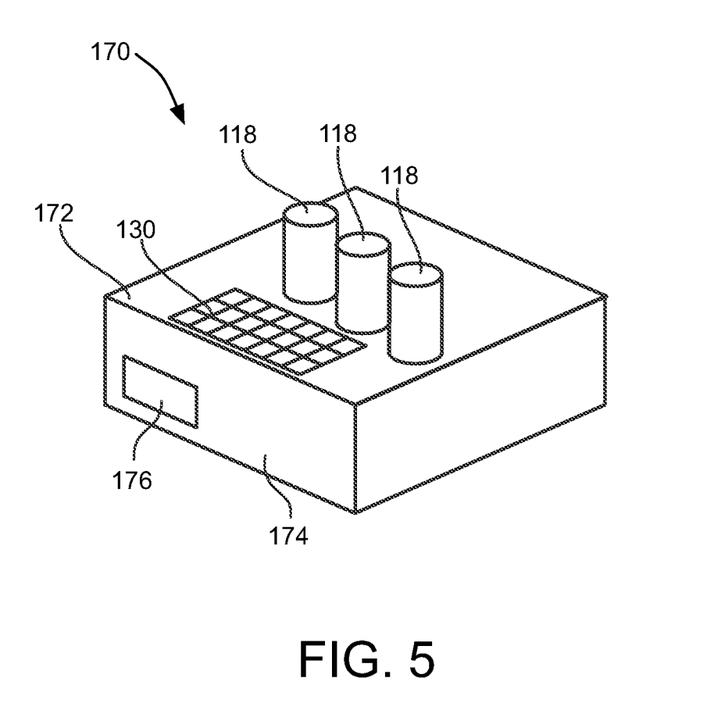
FIG. 5 is an isometric view of an assay kit that may be used with the microplate reader of FIG. 1.

Referring to FIG. 5, in one embodiment, and assay kit 170 includes a container 172, one or more microplates 130, and one or more reagent supplies 118. The assay kit 170 is associated with a particular protocol and the contents of such kit 170 are selected in accordance with such protocol. Disposed on a face 174 of the container 172 is an assay kit NFC tag 176. The assay kit NFC tag 176 has stored therein data that identifies the protocol with which the assay kit 170 may be used, the contents of the assay kit 170, and the quantity of each reagent supply 118 available in the assay kit 170.

Figure 6:
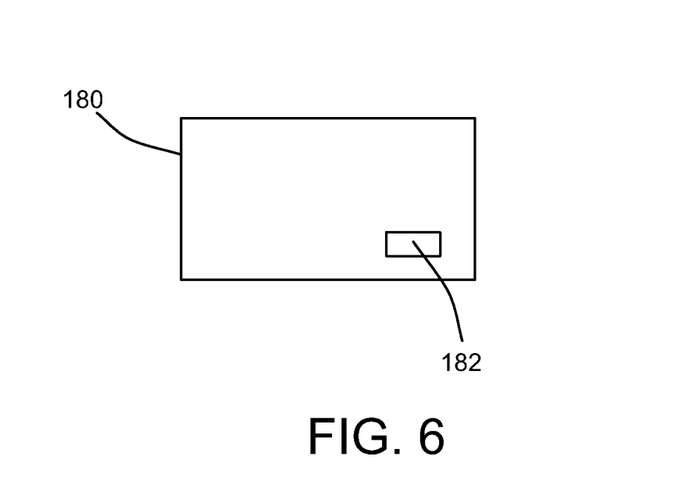
FIG. 6 is a planar view of a user access card that may be used with the microplate reader of FIG. 1.

Referring to FIG. 6, in one embodiment, an authorized user of the microplate reader 100 may be issued an identification card or access card 180 that includes a user NFC tag 182. The user NFC tag 182 includes information that identifies the user. The card 180 may have indicia (not shown) imprinted thereon that also provides information about the user.

Figure 7A:
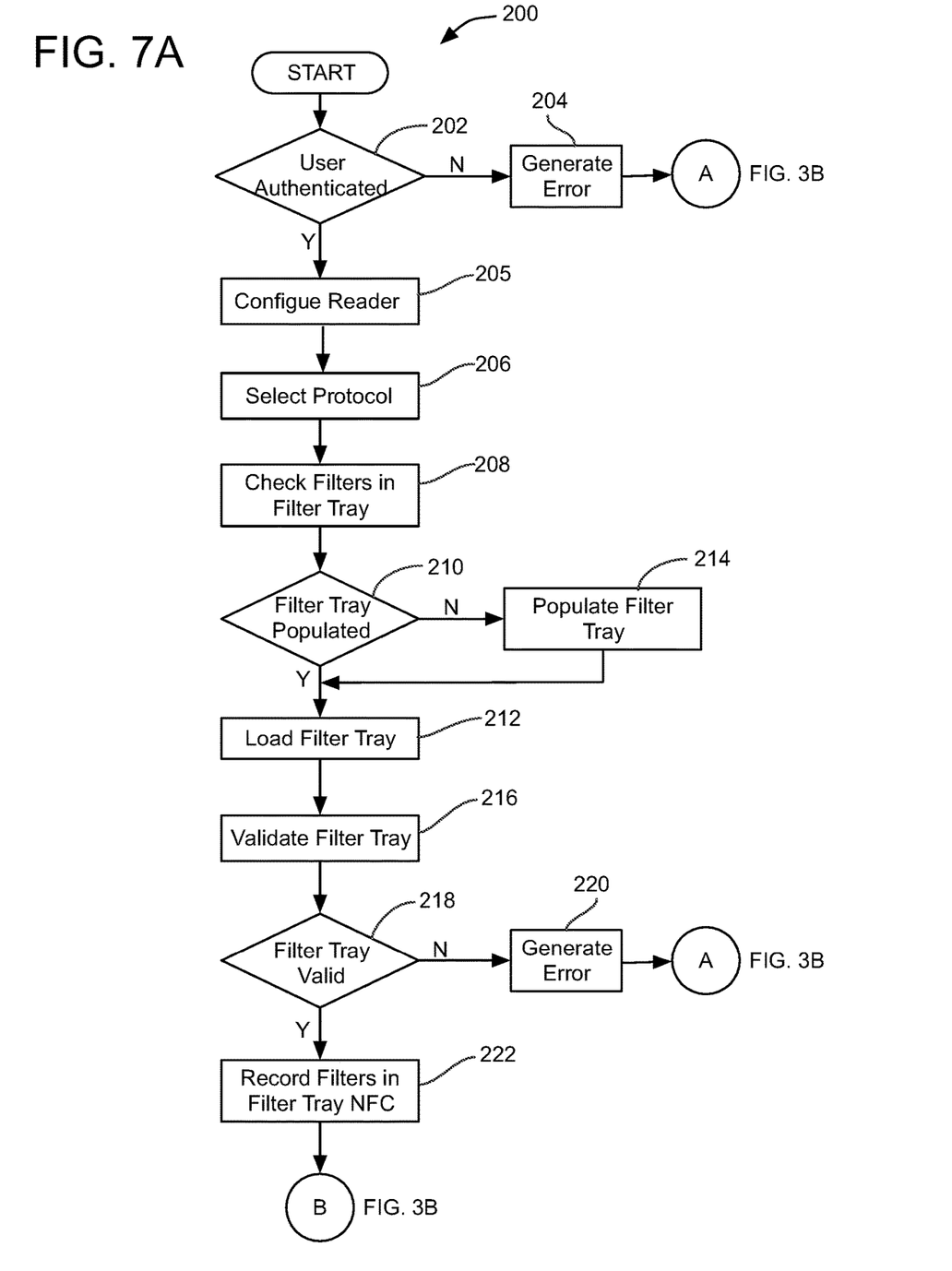
FIGS. 7A and 7B are flowcharts of processing undertaken by a controller of the microplate reader of FIG. 1.
Figure 7B:
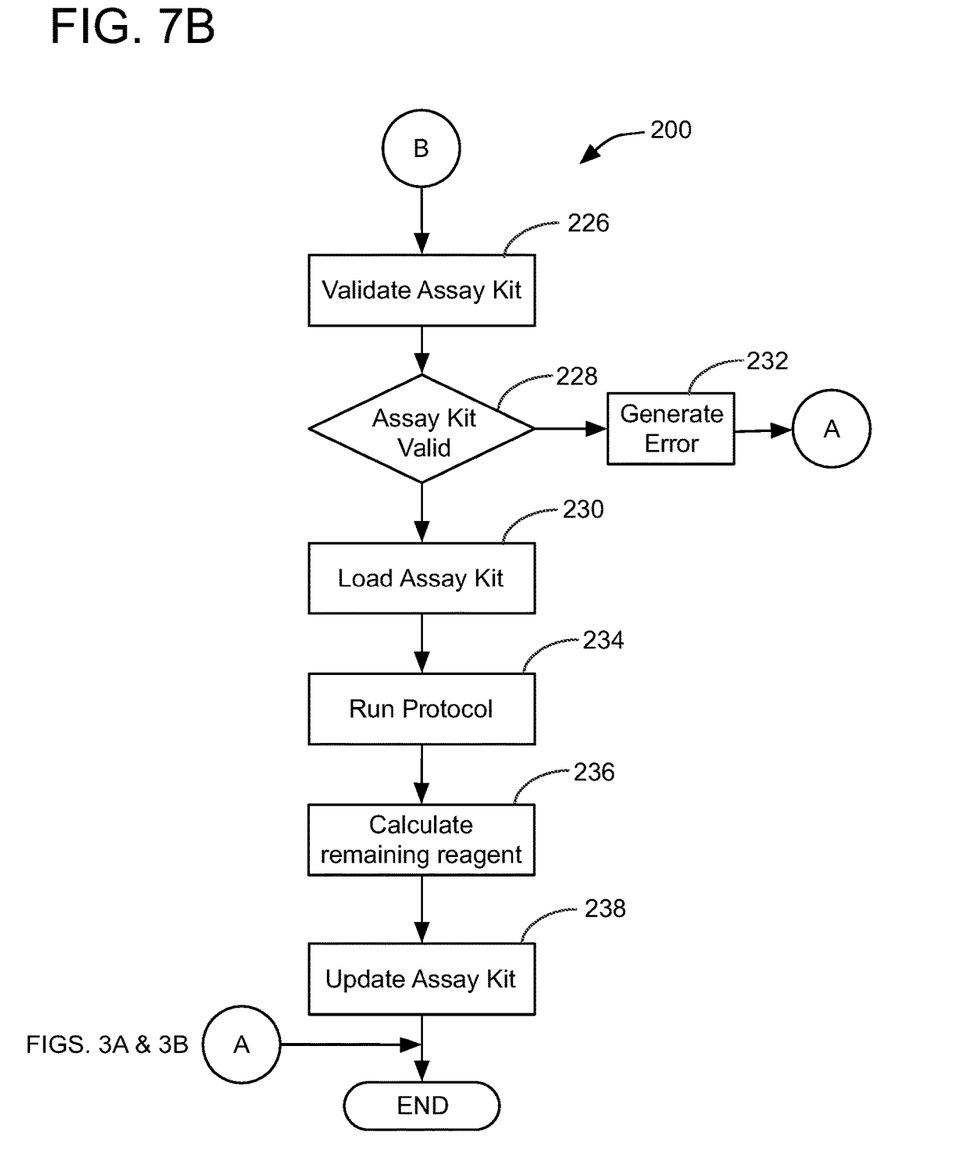

Referring to FIGS. 7A and 7B, in one embodiment, the controller 108 undertakes the processing illustrated in the flowchart 200 to operate the microplate reader 100. Referring to FIGS. 1-6 and 7A, at step 202, the controller 108 determines whether a user is allowed to use the microplate reader 100. In particular, the controller 108 prompts the user (e.g., via the display 104) to present the access card 180 such that the first NFC reader/writer 106 communicates with the user NFC tag 182 to read the information stored therein. In some embodiments, the user contacts the user NFC tag 108 with the first NFC reader/writer 106. In other embodiments, the user brings the user NFC tag 108 within a predetermined distance of the NFC reader/writer 106.

The controller 108 compares the information read from the user NFC tag 182 with information stored in a user database to determine whether the user associated with the access card 180 has sufficient privileges to access the microplate reader 100. The user database may be stored in a storage device (not shown) local to the controller 108, or in a storage device (not shown) the controller access over a local area network or a wide area network.

If at step 202, the controller determines that the user does not have sufficient privileges to use the microplate reader 100, the controller 108 generates an error message on the display that indicates that the user does not have sufficient privileges, at step 204, and exits.

Otherwise, at step 205 the controller 108 configures the microplate reader 100. In some embodiments, the user NFC tag 182 may have user specific configuration information stored therein such as, for example, access information; and the controller 108 configures the microplate reader 100 in accordance with such configuration information.

Then, at step 206, the controller 108 displays on the display 104 a list of the protocols the user may undertake using the microplate reader 100, and receives from the user a selection of one of the protocols either by touching an appropriate region of the display 104 (if such display allows touch input) or by using another input device associated with the controller 108. The protocol specifies, for example, the type of microplate 130 to be used including the number of wells 136 (e.g., 96 wells, 384 wells, etc.) in such microplate 130. The protocol also specifies how the microplate reader 100 is to be used to undertake the protocol including one or more of excitation filter(s), emission filter(s), read height, light source(s), detection system setup (e.g., integration time), volume of reagent to be injected in each well 136, whether the plate should be shaken before measurement, how many times each well should be measured, and the like.

At step 208, the controller 108 allows the user to confirm that the filter tray 132 is populated with the correct filters. In particular, the controller 108 requests, via the display 104, that the user bring the filter tray NFC tag 164 proximate or in contact with the first NFC reader/writer 106. The first NFC reader/writer 106 reads information in the filter NFC tag 164 that identifies each filter 134 loaded in the filter tray 132, and the controller 108 compares such information to the filters required by the protocol. Such identification information may include, for example, wavelength, type, bandwidth, position in the filter tray, applications, and the like. The term "applications" in this context refers to the types of applications the filter may be used such as, for example, absorbance, fluorescence, luminescence, time resolved fluorescence, and the like. Some filters may be appropriate for use in only type or application and other filters may be used for multiple applications.

If at step 210 the controller 108 determines that the filter tray 132 is populated with filters 134 necessary for the protocol the controller proceeds to step 212. Otherwise, at step 214, the controller 108 displays a list of the necessary filters 132 and requests that the user populate the filter tray 132 accordingly, and then proceeds to step 212.

At step 212 the user is asked to load the filter tray 132 into the microplate reader 100.

In some embodiments, the user may simply load the filter tray 132 into the microplate reader 100 without first confirming the filters 134 loaded in the filter tray 132. In such cases, the controller may bypass steps 208, 210, and 214 described above and proceed directly from step 206 to step 212. This may occur for example, if the filter tray 132 is already loaded into the microplate reader 100 from previous operation or if the user believes the filter tray 132 is populated with the correct filters 134.

After the filter tray 132 is loaded, the controller 108 validates the filter tray 132 at step 216. In particular, the controller 108 operates the filter positioning device 124 so that the filter NFC tag 154 of each filter 134 is sequentially brought proximate the second NFC reader/writer 126. The second NFC reader/writer 126 reads the information from each such filter NFC tag 154, and the controller 108 uses such read information to identify the filters 134 that are loaded in the filter tray 134, and compares the identities of such filters with those specified by the selected protocol. In some embodiments, the protocol identifies a filter part number or SKU number, and the controller compares the part number or SKU number read from the filter NFC tag 154 of the filter 132 with that in the protocol to determine if the filter may be used with the protocol.

If at step 218 the controller determines that the filters 134 specified by the selected protocol have not been loaded in the filter tray 132, the controller generates an error at step 220, and exits.

Otherwise, at step 222, the controller 108 directs the second NFC reader/writer 126 to write to the filter tray NFC tag 162 of the filter tray 132 information that identifies each filter 134 loaded in the filter tray 132.

Referring to FIGS. 1-6 and 7B, at step 224, the controller 108 validates the assay kit 170 to make sure the correct assay kit 170 necessary for the protocol is being used. In particular, the controller 108 asks the user to bring the assay kit NFC tag 176 in contact with or proximate to the first NFC reader/writer 106. The NFC reader/writer 106 reads the information from the assay kit NFC tag 176 regarding the contents of the assay kit 170. Such information may include the reagent supplies 118 in the assay kit, the available quantity of reagent available in each reagent supply 118, and the microplate 130 in the assay kit 170. In some embodiments, information is initially written into the assay kit NFC tab 176 when the assay kit 170 is compiled or manufactured. Such information may be updated as described below after the assay kit 170 is used.

If, at step 228, the controller 108 determines that the assay kit 170 contains the necessary components and that sufficient quantities of reagent are available to carry out the selected protocol, the controller 108 proceeds to step 230. Otherwise, at step 232, the controller 108 generates an error notifying the user why the assay kit 170 cannot be used with the protocol and exits.

At step 232, the controller 108 directs the user to load the components of the assay kit 170 into the microplate reader 100. At step 234, the controller 108 operates the illumination source 114, the one or more micropipettes 120, the micropipette actuation device 122, the filter tray positioning device 124, and the sensor 128 as described above to run the selected protocol and record the readings may by the sensor 128.

At step 236, the controller 108 determines the amount of reagent remaining in each reagent supply 118 based on the amount of reagent that was used to run the protocol at step 234.

At step 238, the controller 108 directs the user to remove the components of the assay kit 170, and to bring the assay kit NFC tag 176 into contact with or proximate the first NFC reader/writer 106. The controller 108 then uses the first NFC reader/writer 106 to update the information in the assay kit NFC tag 176 regarding the quantity of reagent that remains in each reagent supply 118. Further, in some embodiments, if an insufficient quantity of reagent remains in any reagent supply 118 to run another protocol, the controller 108 may notify the user to order additional reagent.

After updating the information stored in the assay kit NFC tag 176, the controller 108 exits.

Figure 8:
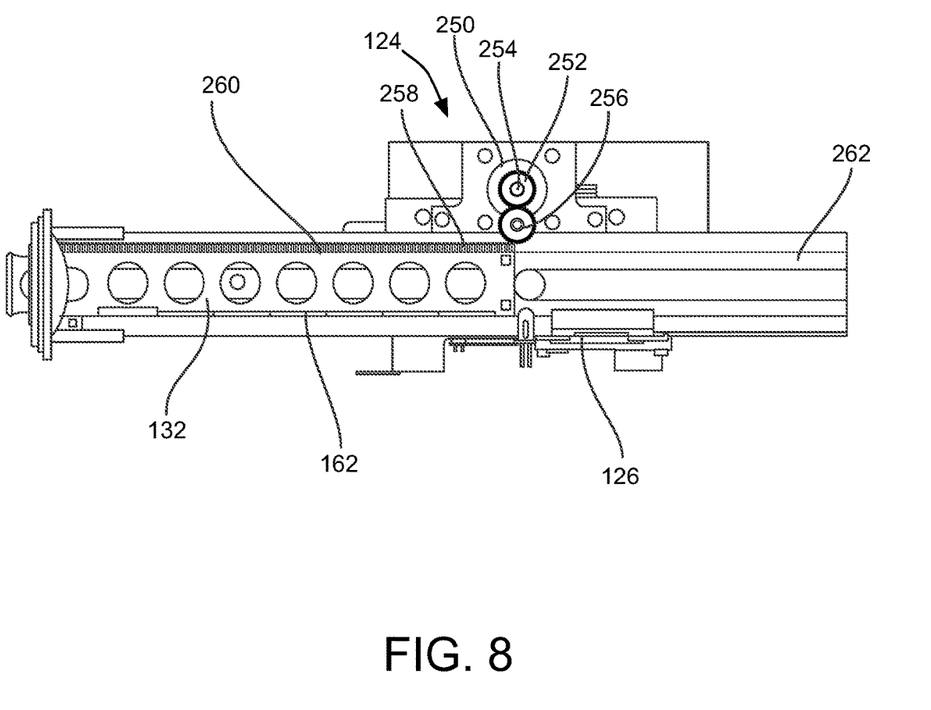
FIG. 8 is top planar view of a filter tray position device of the microplate reader of FIG. 1.

Referring to FIG. 8, one embodiment of the filter tray positioning device 124 includes a drive motor 250 operated by the controller 108, a first gear 252 attached to a spindle 254 of the drive motor 250, and a second gear 256 driven by the first gear 252. A linear gear 258 is secured to a face 260 opposite the face 162 of the filter tray 132. The filter tray 132 is disposed in the microplate reader 100 such that a bottom portion (not shown) of the filter tray 132 engages a fixed rail 262 of the filter tray positioning device 124, and that the second gear 256 engages the linear gear 258 in a rack and pinion manner. Rotation of the spindle 254 of the drive motor 250 causes rotation of the first gear 252, which in turn causes rotation of the second gear 256. The rotation of the second gear 256 causes the linear gear 256, and therefor the filter tray 132, to traverse linearly along the rail 262. The second NFC reader/writer 126 is securely positioned adjacent the rail 262 such that the filter NFC tags 154 of any filters 134 disposed in the filter tray 132 and the filter tray NFC tag 162 pass proximate the second NFC reader/writer 126, and thus be read thereby, as the filter tray moves linearly along the rail 262.

Figure 9:
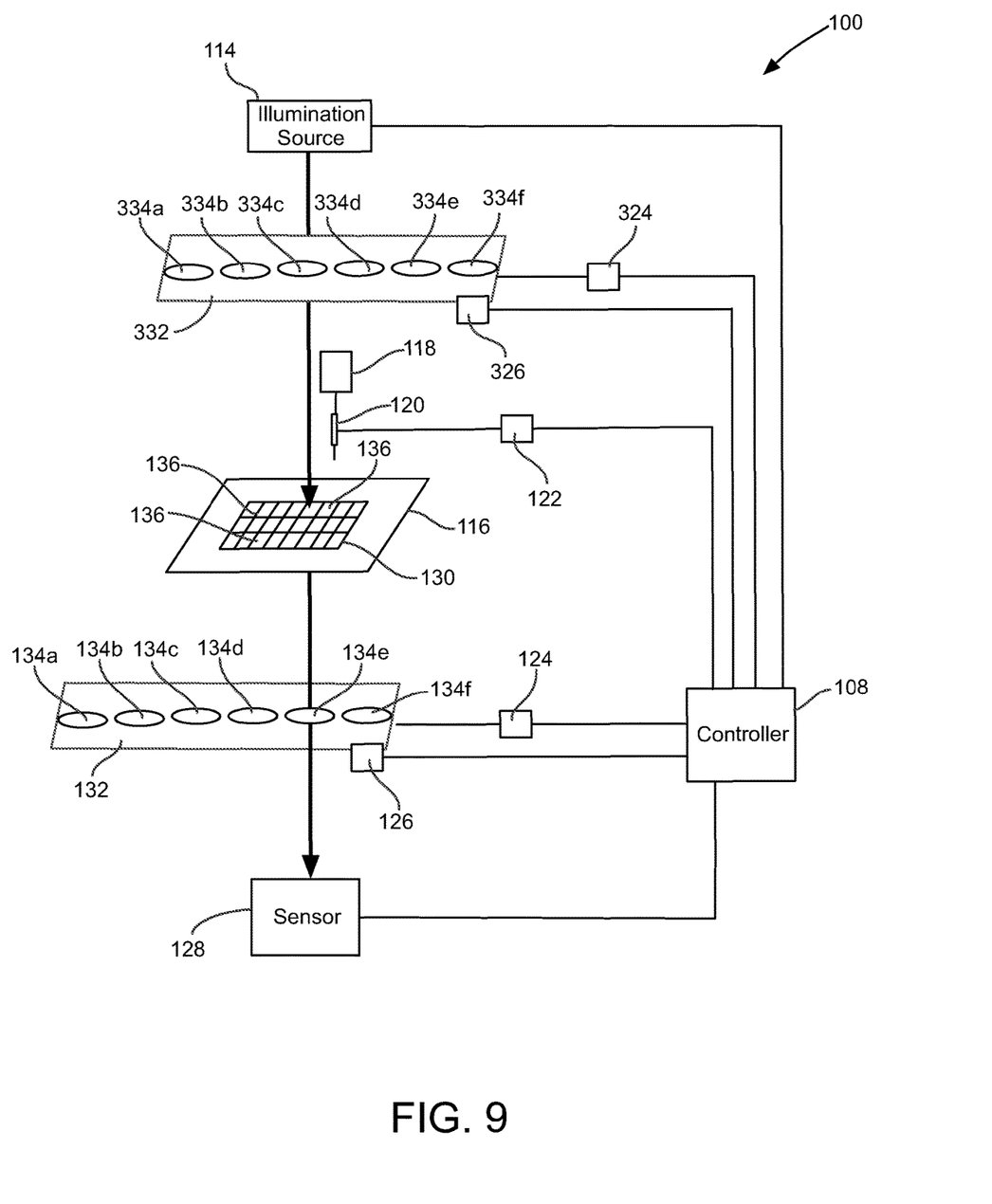
FIG. 9 is a block diagram of another embodiment of the microplate reader of FIG. 1.

Referring to FIG. 9, another embodiment of the microplate reader 100 may include the use of the filter tray 132 disposed in the light path between the microplate 130 and the one or more sensor(s) 128, and a further filter tray 332 disposed in the light path between the illumination source 114 and the microplate 130. The filter tray 332 is populated with one or more filters 334a, 334b, . . . , and 334e. The controller may operate a further filter tray positioning device 324 to selectively position one of the filters 334 of the filter tray 332 in the light path between the illumination source and the microplate 130. The filter tray 332 and the filters 334 are substantially identical to the filter tray 132 and filters 134 described above. In particular, the filter tray 332 includes a filter tray NFC tag 164 and each filter 334 disposed therein includes a filter NFC tag 154 as described above.

The microplate reader 100 shown in FIG. 9 also includes a further NFC reader/writer 326 for reading information from and writing information to the filter tray NFC tag 164 of the filter tray 334, and reading information from the filter NFC tag 154 associated with each filter 332 disposed in such filter tray 334. Referring also to FIG. 7A, with respect to the microplate reader 100 that uses two filter trays, the controller undertakes steps 208-216 described above with both the filter tray 132 and the filter tray 332.

Although the microplate reader 100 described in the foregoing disclosure uses a filter tray 132, it should be apparent that the system and processes described above may be readily adapted for use with a microplate reader that uses a filter wheel. For example, the filter tray NFC tag 164 may be attached to a filter wheel and the operation of the controller 108, the first NFC reader/writer, and the second NFC reader/writer 126 would be substantially unchanged.

The use of NFC readers to track components necessary for a protocol described above are presented in the context of operating the microplate reader 100. However, it should be apparent to one who has ordinary skill in the art that the disclosed readers and processes may be readily adapted for use with other types of instruments in which particular components (such as filters and/or reagents) are needed for proper operation.

INDUSTRIAL APPLICABILITY

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. It should be understood that the illustrated embodiments are exemplary only, and should not be taken as limiting the scope of the disclosure.

What is claimed is:

1. A microplate reader comprising:
   a housing;
   a first NFC reader/writer;
   a filter tray positioning device;
   a filter tray, wherein a filter tray has an NFC tag disposed thereon;
   a first optical filter disposed in the filter tray, wherein the first optical filter has disposed adjacent thereto a first filter NFC tag on the filter tray; and a controller, wherein the controller receives information about an assay protocol to be undertaken, wherein the assay protocol specifies a filter to be used;

wherein the first NFC reader/writer reads first filter information stored in the first filter NFC tag, the controller directs the first NFC reader/writer to store the first filter information in the filter tray NFC tag, and the controller enables operation of the microplate reader to undertake the assay protocol only if the first filter information indicates that the first optical filter is in accordance with the filter specified by the assay protocol.

2. The microplate reader of claim 1, further including a second NFC reader/writer, wherein the first NFC reader/writer reads an NFC tag inside the housing and the second NFC reader/writer reads an NFC tag outside the housing.

3. The microplate reader of claim 2, further including a display, wherein the second NFC reader/writer reads filter tray information from the filter tray NFC tag and the controller displays the filter tray information on the display.

4. The microplate reader of claim 2, further comprising an assay kit, wherein the assay kit includes an assay kit NFC tag, the second NFC reader/writer reads assay kit information from the assay kit NFC tag, and the controller enables operation of the microplate reader to undertake the assay protocol only if the assay kit information indicates that the assay kit is in accordance with an assay kit specified by the assay protocol.

5. The microplate reader of claim 4, wherein the assay kit includes a reagent, the assay kit information includes information regarding an amount of the reagent in the assay kit, and the controller enables operation of the microplate reader to undertake the assay protocol only if the amount of the reagent is in accordance with an amount specified by the assay protocol.

6. The microplate reader of claim 5, wherein after operation of the microplate reader to undertake the assay protocol, the controller determines an amount of remaining reagent and the controller directs the second NFC reader/writer to record information including the amount of the remaining reagent in the assay kit NFC tag.

7. The microplate reader of claim 1, wherein the filter tray positioning device moves the filter tray along a linear path, and the first NFC reader/writer is disposed such that as the filter tray is moved by the filter tray positioning device, the filter tray NFC tag and the first filter NFC tag pass adjacent the first NFC reader/writer.

8. The microplate reader of claim 1, further including a filter housing, wherein the first optical filter is disposed in the filter housing, and the filter housing is disposed in the filter tray.

9. The microplate reader of claim 1, further including a second optical filter disposed in the filter tray, and a second filter NFC tag, wherein the first NFC reader/writer reads second filter information from the second filter NFC tag, and the controller directs the first NFC reader/writer to store the second filter information in the filter tray NFC tag.

10. The microplate reader of claim 1, further including an input device, and the controller receives a selection of the assay protocol from a plurality of protocols.

11. A method of operating microplate reader, wherein the microplate reader includes a housing, a first NFC reader/writer, and a filter tray positioning device comprising:

disposing a filter tray in the microplate reader, wherein the filter tray has an NFC tag disposed thereon;

disposing a first optical filter disposed in the filter tray, wherein the first optical filter has disposed adjacent thereto a first filter NFC tag on the filter tray; and receiving by a controller information about an assay protocol to be undertaken, wherein the assay protocol specifies a filter to be used;

reading first filter information stored in the first filter NFC tag;

operating the first NFC reader/writer to store the first filter information in the first filter tray NFC tag;

operating the microplate reader to undertake the assay protocol only if the first filter information indicates that the first optical filter is in accordance with the filter specified by the assay protocol.

12. The method of claim 11, wherein operating the first NFC reader/writer includes operating the NFC reader/writer to read information from an NFC tag disposed inside the housing and further including operating a second NFC reader/writer to read information from an NFC tag disposed outside the housing.

13. The method of claim 12, further including reading with the second NFC reader/writer filter tray information from the filter tray NFC tag and displaying the filter tray information on a display.

14. The method of claim 13, further including reading using the second NFC reader/writer assay kit information from an assay kit NFC tag disposed on an assay kit, and enabling operation of the microplate reader to undertake the assay protocol only if the assay kit information indicates that the assay kit is in accordance with an assay kit specified by the assay protocol.

15. The method claim 14, wherein the assay kit information includes information regarding an amount of a reagent in the assay kit, and enabling operation of the microplate reader to undertake the assay protocol only if the amount of the reagent is in accordance with an amount specified by the assay protocol.

16. The method of claim 15, further including operating the microplate reader to undertake the assay protocol, and determining after such operation an amount of remaining reagent, and the controller directs the second NFC reader/writer to record information including the amount of the remaining reagent in the assay kit NFC tag.

17. The method of claim 11, further including moving the filter tray along a linear path, and disposing the first NFC reader/writer such that as the filter tray is moved by the filter tray positioning device, the filter tray NFC tag and the first filter NFC tag pass adjacent the first NFC reader/writer.

18. The method of claim 11, further including disposing the first optical filter in a filter housing, and disposing the filter housing in the filter tray.

19. The method of claim 11, further including disposing a second optical filter in the filter tray, and reading second filter information from a second filter NFC tag, and directing the first NFC reader/writer to store the second filter information in the filter tray NFC tag.

20. The method of claim 11, further including receiving a selection of the assay protocol from a plurality of protocols.

* * * * *